(12) United States Patent
Gupta et al.

(10) Patent No.: US 12,111,284 B2
(45) Date of Patent: Oct. 8, 2024

(54) GAS SENSORS WITH NEGLIGIBLE RESPONSE TO HUMIDITY AND TEMPERATURE

(71) Applicant: The Regents of the University of California, Oakland, CA (US)

(72) Inventors: Niharika Gupta, Berkeley, CA (US); Ali Javey, Lafayette, CA (US); Hossain Mohammad Fahad, Berkley, CA (US)

(73) Assignee: The Regents of the University of California, Oakland, CA (US)

(*) Notice: Subject to any disclaimer, the term of this patent is extended or adjusted under 35 U.S.C. 154(b) by 445 days.

(21) Appl. No.: 17/594,605

(22) PCT Filed: Apr. 23, 2020

(86) PCT No.: PCT/US2020/029632
§ 371 (c)(1),
(2) Date: Oct. 22, 2021

(87) PCT Pub. No.: WO2020/219758
PCT Pub. Date: Oct. 29, 2020

(65) Prior Publication Data
US 2022/0205947 A1 Jun. 30, 2022

Related U.S. Application Data

(60) Provisional application No. 62/837,839, filed on Apr. 24, 2019.

(51) Int. Cl.
*G01N 27/403* (2006.01)
*G01N 27/414* (2006.01)
*G01N 33/00* (2006.01)

(52) U.S. Cl.
CPC ..... *G01N 27/4141* (2013.01); *G01N 27/4146* (2013.01); *G01N 33/0037* (2013.01)

(58) Field of Classification Search
CPC .......... G01N 27/4141; G01N 27/4146; G01N 33/0037; G01N 27/14; G01N 2035/00346; G01N 21/3504; G01N 33/0009
See application file for complete search history.

(56) References Cited

U.S. PATENT DOCUMENTS

| | | | | |
|---|---|---|---|---|
| 5,480,829 A | * | 1/1996 | Abrokwah | ........ H01L 29/66462 438/188 |
| 6,111,280 A | * | 8/2000 | Gardner | ............... G01N 27/128 257/253 |
| 2005/0029250 A1 | * | 2/2005 | Niwa | ................... F02D 41/1494 219/494 |

(Continued)

OTHER PUBLICATIONS

Soulantica, et al. "Synthesis of indium and indium oxide nanoparticles from indium cyclopentadienyl precursor and their application for gas sensing." Advanced Functional Materials 13.7 (Jul. 4, 2003): 553-557.

(Continued)

*Primary Examiner* — Niki H Nguyen

(57) ABSTRACT

In one example, a gas sensor is provided. The gas sensor includes a substrate, an isolation region formed on outer edges of the substrate, a micro-heater formed on the isolation region, a sensing layer formed on the substrate inside of the isolation region, and a source and drain formed around the sensing layer and inside of the isolation region.

15 Claims, 14 Drawing Sheets

(56) References Cited

U.S. PATENT DOCUMENTS

2006/0154401 A1    7/2006  Gardner et al.
2010/0170888 A1    7/2010  Lee et al.

OTHER PUBLICATIONS

Salomonsson, et al. "Hydrogen interaction with platinum and palladium metal-insulatorsemiconductor devices." Journal of Applied Physics 98.1 (Jul. 1, 2005).
Park, et al. "Fabrication of a superhydrophobic and oleophobic PTFE membrane: An application to selective gas permeation." Materials Research Bulletin 83 (Nov. 1, 2016): 88-95.
Gupta, et al. "Elimination of Response to Relative Humidity Changes in Chemical-Sensitive Field-Effect Transistors." ACS sensors 4.7 (& May 2019) 1857-1863.
Yuan, et al. "Trace-Level, Multi-Gas Detection for Food Quality Assessment Based on Decorated Silicon Transistor Arrays." Advanced Materials 32.21 (May 25, 2020).
PCT International Search Report and Written Opinion for PCT/US20/29632 (Oct. 6, 2020) 15 pages.

\* cited by examiner

GAS SENSORS WITH NEGLIGIBLE RESPONSE TO HUMIDITY AND TEMPERATURE

CROSS REFERENCE TO RELATED APPLICATIONS

This application is a national stage application, filed under 35 U.S.C. 371, of International Patent Application No. PCT/US2020/029632, filed on Apr. 23, 2020, which claims priority to U.S. Provisional Patent Application Ser. No. 62/837,839, filed Apr. 24, 2019, which is herein incorporated by reference in its entirety.

FIELD OF THE INVENTION

The present disclosure relates generally to gas sensors.

BACKGROUND

Selectivity refers to the ability of a gas sensor to respond selectively to one or more analytes and depends, in part, on the insensitivity of the gas sensor to ambient relative humidity and temperature changes. The sensitivity to these ubiquitous variations is currently the major limiting factor of important gas sensing applications such as air-quality monitoring and medical diagnostics. The fact that most of the active sensing materials of a gas sensor interact with water makes achieving humidity insensitivity a challenge. Responsiveness of chemical or gas sensors to even the slightest environmental changes leads to inaccurate detection of gas and/or interpretation of gas concentration, and, in turn, deviated sensor signals. Therefore, elimination of humidity and temperature sensitivity is essential to having a robust and precise sensor signal.

Research into making gas sensors humidity and temperature insensitive can be divided into two strategies: computational methods and experimental methods. Computational methods involve signal processing utilizing data from humidity and temperature sensors along with sensor data at different concentrations in different humidity and temperature levels to calculate exact gas concentration. Multivariate calibration methods such as principal component regression (PCR), partial least square (PLS) and artificial neural networks (ANN) have been utilized to compensate for the sensor response to humidity changes. The need for huge data sets to train the ANN and linear data sets in other methods makes computation methods disadvantageous because of the complexity of calibration required for different combinations of relative humidity and temperature. Additionally, both humidity sensors and temperature sensors would need to have selective signal responses with respect to each other, which is experimentally impractical to achieve and would need further post-processing, which in turn adds to the calibration complexity.

Experimental methods include functionalization with hydrophobic materials and modifications to the active sensing material either by annealing, doping, or specialized growth conditions. These techniques decrease the sites available for water interaction, thereby reducing the response of the sensor to humidity. However, previous work studying these techniques has not been able to fully eliminate the response to humidity variations and focus on either response to gas in different humidity levels or the response to varying humidity. Nor has the previous work considered response to gas in different humidity levels and response to varying humidity as a combined problem. The dominant technology for gas sensing, metal oxide semiconductor (MOS) sensors is humidity insensitive due to high operating temperature (e.g., >200° C.), which boils off any water molecule on the active sensing part; however, the high temperatures make MOS sensors disadvantageous in consumer electronics applications due to power consumption and safety issues.

SUMMARY

According to aspects illustrated herein, there is provided a gas sensor. One disclosed feature of the embodiments is a gas sensor that includes a substrate, an isolation region formed on outer edges of the substrate, a micro-heater formed on the isolation region, a sensing layer formed on the substrate inside of the isolation region, and a source and drain formed around the sensing layer and inside of the isolation region.

In another aspect, the present disclosure provides a method for fabricated a gas sensor. The method includes providing a substrate, forming a silicon dioxide isolation region on outer edges of the substrate, doping source and drain regions on the substrate, patterning a sensing layer region between the source and drain regions, doping the sensing layer region, defining source and drain contacts on the source and drain regions, wherein the source and drain contacts comprise a layer of nickel and tungsten, forming a tungsten micro-heater on the silicon dioxide isolation region, and depositing a sensing layer on the sensing layer region.

BRIEF DESCRIPTION OF THE DRAWINGS

The teaching of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

The present disclosure provides a gas sensor and method for producing the same that is insensitive to humidity and/or temperature changes. As noted above, elimination of humidity and/or temperature sensitivity can lead to a better gas sensor. Current methods and sensors may use computational or experimental methods to minimize humidity and temperature sensitivity. However, these current methods may be computational intensive, have high power consumption, and/or have safety issues at the high temperatures required to remove sensitivity to humidity.

In the present disclosure, a gas sensor that can eliminate sensor response to variations to relative humidity and/or temperature is provided. The gas sensor may be fabricated using chemical-sensitive field effect transistors (CS-FETs) with micro-heaters. CS-FETs are nanoscale silicon transistors in which the electrical gate is replaced by a chemical sensing layer consisting of nanoparticles.

The work-function and/or morphology of the sensing layer changes upon exposure to target chemical species, resulting in strong output drain current modulation and enabling high detection sensitivity. In the past, the micro-heaters were pulsed immediately after the detection of target gas, which resulted in dramatically improved recovery times. Unlike previous methods or sensor designs with bulk silicon CS-FETs, the present disclosure uses the integration of local on-chip micro-heaters around the sensors.

Figure 1:
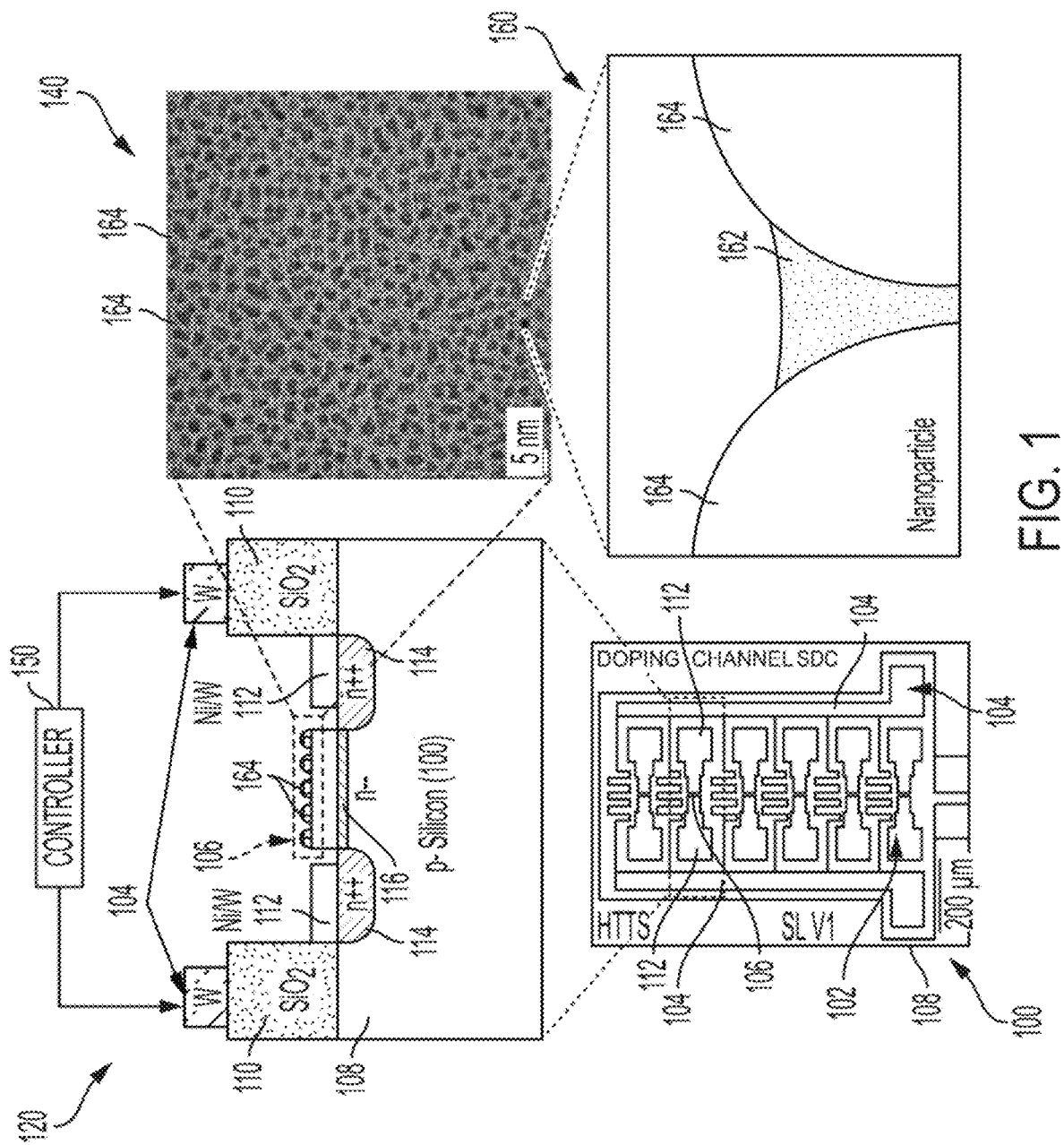
FIG. 1 illustrates an example cross-sectional view of a gas sensor of the present disclosure.

FIG. 1 illustrates an example gas sensor 102 of the present disclosure. FIG. 1 illustrates a top view 100 of the gas sensors 102, a cross-sectional view 120 of a gas sensor 102, a close-up view 140 of a sensor layer 106, and a close-up view 160 of capillary condensation of water 162 occurring in a cavity between nano-particles 164. In one embodiment, one or more of the gas sensors 102 may be formed on a substrate 108. The substrate 108 may be a silicon substrate. The silicon may comprise prime grade silicon wafers with a sheet resistivity in the range of 10-20 ohms-centimeters ($\Omega \cdot cm$). The combination of the gas sensors 102 and the substrate 108 may also be referred to herein as a "chip," a "gas sensing device," a "CS-FET," and the like.

In one embodiment, each gas sensor 102 may include a micro-heater 104 formed on top of an isolation region 110 (shown in view 120). The isolation regions 110 may include grown and patterned silicon dioxide. The micro-heaters 104 may be formed from tungsten (W) and operated at a constant voltage to maintain a desired power output and to heat the substrate 108 and gas sensors 102 to a desired temperature. The desired temperature may allow the gas sensor 102 to be insensitive to changes in humidity and/or changes in ambient temperature. The operating parameters are discussed in further details below.

In one embodiment, a controller 150 may be electronically coupled to the micro-heaters 104 to control operation of the micro-heaters 104. In addition, a temperature sensor (not shown) may be added to the chip and connected to the controller 150. The controller 150 may adjust an amount of power (e.g., by regulating current to maintain a constant voltage) in response to changes in ambient temperature. As a result, the controller 150 may help to regulate the temperature, or to maintain a constant operating temperature (as measured by the temperature sensor) of the gas sensors 102 to ensure that the gas sensors 102 are insensitive to changes in humidity and/or temperature.

In one embodiment, the gas sensors 102 may include source and drain contacts 112 formed on top of source and drain regions 114 (shown in view 120). The source and drain regions 114 may be n-type doped or p-type doped regions. In one embodiment, the source and drain regions 114 may be n-type doped with phosphorous. The source and drain contacts 112 may be formed with layers of nickel (Ni) and tungsten (W).

A sensor layer 106 may be formed on top of a sensing layer region 116 located between the source and drain regions 114. In one embodiment, the sensor layer 106 may be formed by depositing nano-particles 164. The view 140 illustrates the dispersion of nano-particles 164 in the sensor layer 106. As discussed in further details below, the nano-particles 164 may create a cavity between the nano-particles 164 that allows for capillary condensation of water 162 in the cavity.

The type of material used for the nano-particles 164 may be a function of a type of gas to be detected by the gas sensor 102. For example, for hydrogen gas detection, the sensor layer 106 may include platinum (Pt) nano-particles on trichloro(1H,1H,2H,2H-perfluorooctyl) silane (FOTS). For nitrogen oxide gas detection, the sensor layer 106 may include indium oxide ($InO_x$) nano-particles. It should be noted that other materials may be used for the sensor layer 106 to detect other gases that are not described herein. The provided examples should not be considered limiting.

In one embodiment, the plurality of gas sensors 102 may include the same type of sensing layer 106 to detect the same gas. In one embodiment, the plurality of gas sensors 102 may include different sensing layers 106 to detect different gases. For example, a first gas sensor 102 may have a sensor layer 106 with Pt/FOTS to detect hydrogen gas, a second gas sensor 102 may have a sensor layer 106 with $InO_x$ to detect nitrogen oxide gas, and so forth. Thus, different gases may be detected by a single gas sensor device.

Figure 2A:
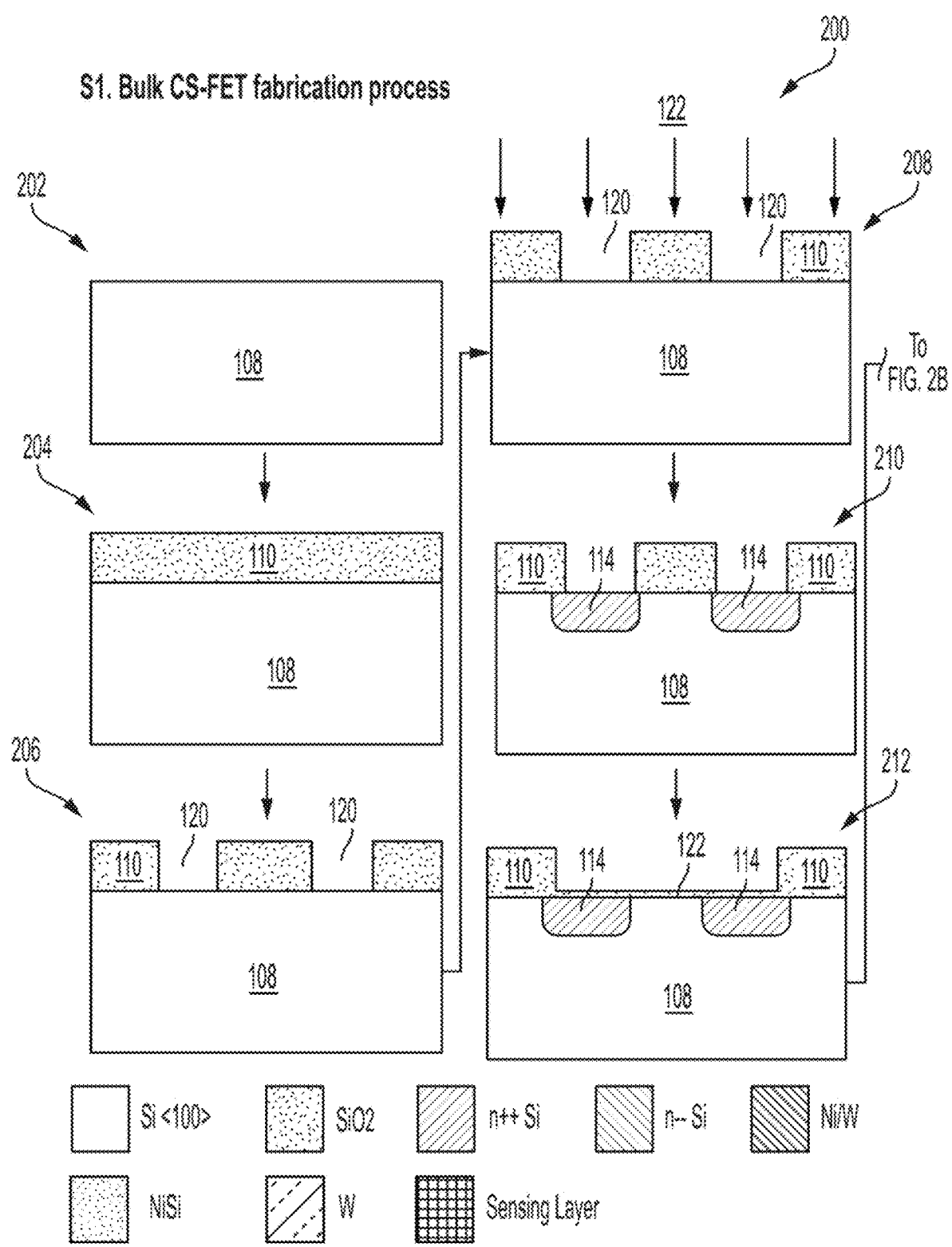
FIGS. 2A-2B illustrate an example process flow diagram of a method to fabricate the gas sensor of the present disclosure.
Figure 2B:
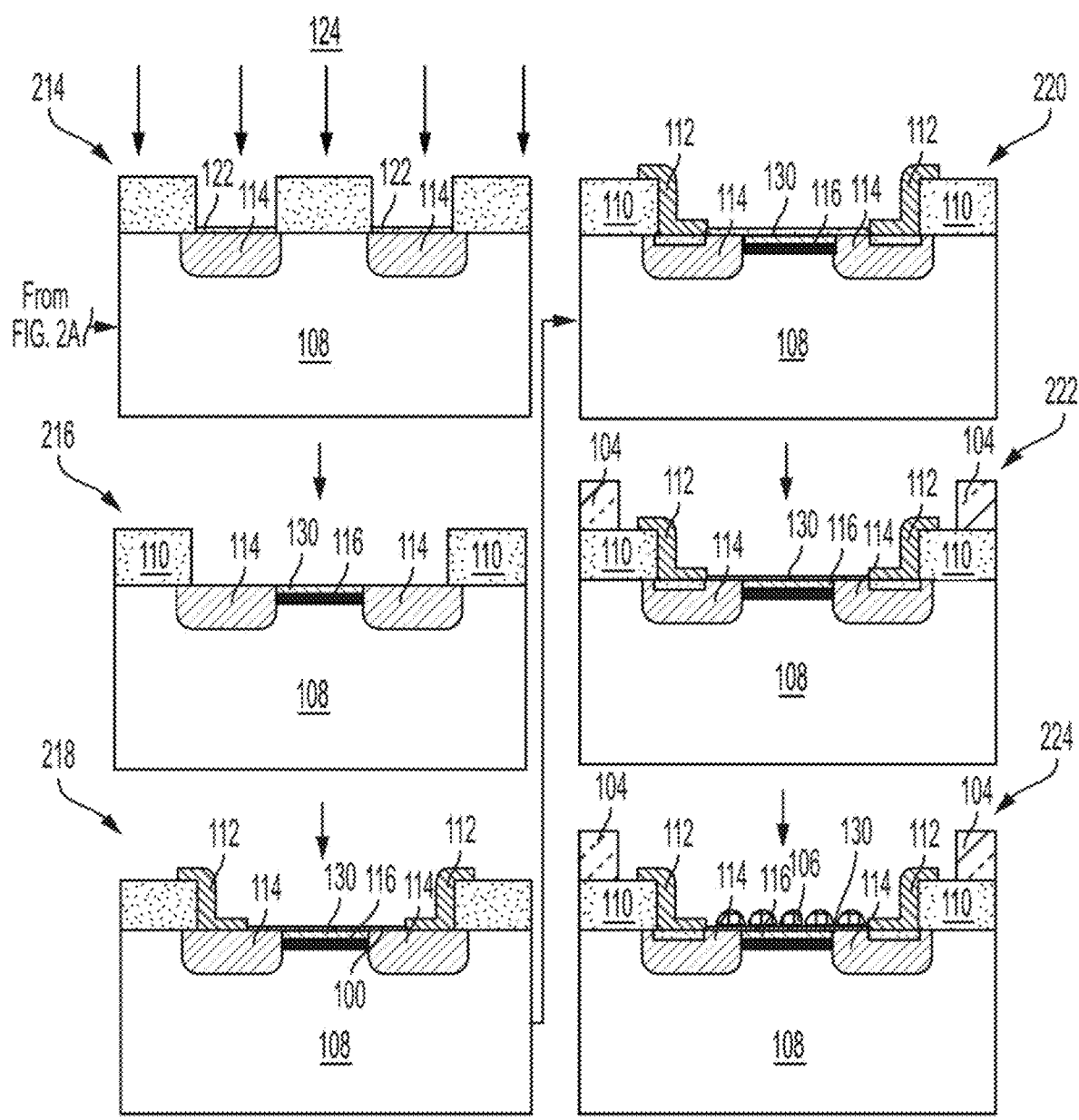

FIGS. 2A-2B illustrate an example process flow diagram for a method 200 of producing or fabricating the gas sensor 102 of the present disclosure. The method 200 may be performed by various tools within a fabrication plant under the control of a central processor or controller that coordinates operation of the tools. Examples of tools that can be used are described herein, but it should be noted that there may be other methods for performing each block of the method 200 that are within the scope of the present disclosure.

The method 200 may begin at block 202. At block 202, a substrate 108 is provided. The substrate 108 may comprise prime grade silicon {100} wafers with sheet resistivity in the range of 10-20 $\Omega \cdot cm$. Before processing, the silicon wafers may be cleaned in a standard piranha bath (e.g., 1:4 hydrogen peroxide/sulfuric acid) at 120 degrees Celsius (° C.). Any native oxide may be removed using a 10 second (s) dip in a 1:10 hydrofluoric acid bath.

At block 204, an isolation region 110 may be formed on the substrate 108. The isolation region 110 may be thermally grown silicon dioxide. The silicon dioxide may be grown to a thickness of approximately 350 nanometers (nm). The silicon dioxide may be grown using a three-step dry (5 minutes), wet (55 minutes), dry (5 minutes) oxidation process at 1000° C. and at atmospheric pressure for 55 minutes. The oxide thickness may be verified using fixed angle ellipsometry.

At block 206, trenches 120 may be etched away to form the source and drain regions. The trenches 120 may be formed using a photolithography process (e.g., pattern, expose, bake, and etch procedure). In one embodiment, the photolithography process may be a standard i-line photolithography process (e.g., Fujifilm, photoresist: OiR 906-12, developer: OPD-4262) and wet etching the isolation oxide (e.g., in a 5:1 buffered hydrofluoric acid for 5 minutes).

At block 208, an ion implantation process 122 may be performed. The ion implantation process 122 may be used to dope portions of the exposed portions of the substrate 108 to form the source and drain regions 114. In one embodiment, the ion implantation may use $4.5e^{14}$ cm$^{-2}$, Phosphorus, 15 KeV.

At block 210, the source and drain regions 114 may be formed. In one embodiment, to complete the formation of n+2 doped regions (e.g., the source and drain regions 114), phosphorous drive-in and activation is performed in the substrate 108 in the source and drain regions 114 by rapid thermal annealing (RTA) at 1050° C. for 30 seconds in nitrogen gas ($N_2$). It should be noted that phosphorous is used for n-type doping. However, other chemicals or compounds may be used for p-type doping.

At block 212, a channel region may be formed using a photolithography and etch process. For example, a mask 122 may be deposited or formed over the source and drain regions 114. The mask 122 may be thermally grown silicon dioxide similar to the silicon dioxide grown for the isolation region 110.

At block 214, the mask 122 may be etched to expose an undoped portion of the substrate 108 between the source and drain regions 114. The exposed portion of the substrate 108 may be doped to form the channel region. The doping may be performed using ion implantation (e.g., $5e^{11}$ cm$^{-2}$, Phosphorus, 18 KeV) and subsequently performing RTA at 900° C. for 1 s in $N_2$.

At block 216, the remaining portions of the mask 122 may be removed or etched away. In addition, a nickel silicide layer 130 may be formed on the channel region 116.

At block 218, the source and drain contacts 112 may be formed. In one embodiment, to define the source and drain contacts 112, a separate source-drain metallization mask may be used. The source-drain metallization mask may underlap the doped source and drain regions by 11 microns (µm). After this, argon may be sputtered to etch the native oxide. Then, 20 nm of nickel and 50 nm of tungsten may be deposited in the source and drain regions 114 using a sputtering tool followed by lift-off in acetone.

At block 220, an anneal process may be performed to complete the nickel silicide layer 130 and the source-drain metallization of the source and drain contacts 112. For example, to achieve ohmic source and drain contacts, nickel silicidation may be performed in forming gas (e.g., 5% hydrogen ($H_2$) in $N_2$) using RTA at 400° C. for 5 minutes.

At block 222, the micro-heaters 104 may be formed on the isolation regions 110. For example, micro-heaters 104 may be patterned using photolithography and sputtering of tungsten. In one embodiment, 200 nm of tungsten may be sputtered.

At block 224, the sensor layer 106 may be deposited. As noted above, the type of material deposited for the sensor layer 106 may be a function of a type of gas that is to be detected by the gas sensor 102. For example, for a hydrogen sensor, FOTS may be deposited using AMST molecular vapor deposition MVD100. Following this, platinum may be deposited by electron beam evaporation of 1 nm of platinum.

In one embodiment, for a nitrogen oxide sensor, $InO_x$ may be deposited by thermal evaporation of 1.5 nm of $InO_x$. Afterwards, the gas sensor 102 may be annealed in forming gas at 150° C. for 1 hour post deposition, which may complete the fabrication process.

Figure 3:
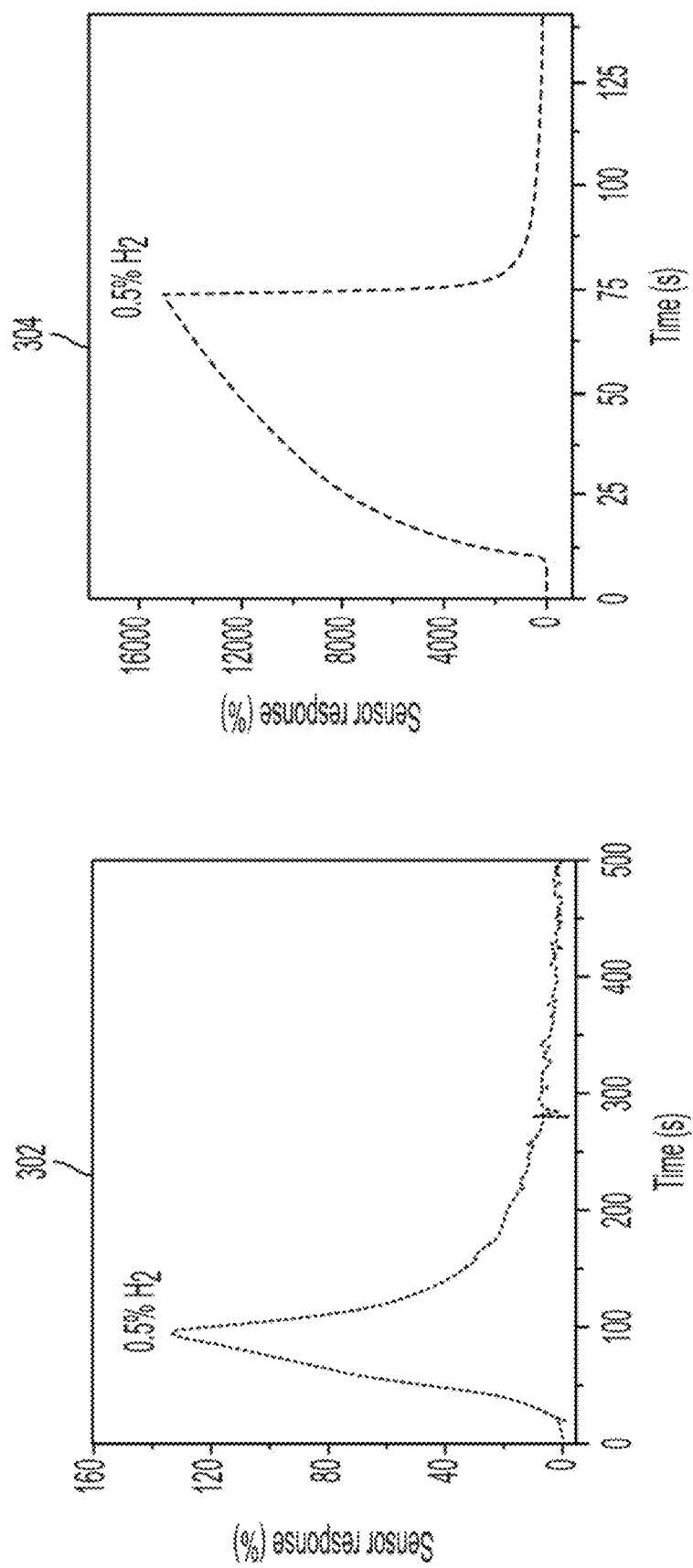
FIG. 3 illustrates an example graph that illustrates $H_2$ sensor response characteristics for an example gas sensor that has a FOTS/Pt sensor layer of the present disclosure.

As noted above, in one embodiment, the sensor layer 106 may be Pt/FOTS as shown in FIG. 1. This layer can be used for the detection of hydrogen gas due to the strong interaction between Pt and hydrogen gas and the enhanced sensor performance characteristics with FOTS underneath Pt, as illustrated by graphs 302 and 304 in FIG. 3. Graph 302 illustrates an example sensor response to 0.5% $H_2$ at room temperature at $V_D$=0.1 Volts (V) with a sensing layer of 1 nm Pt CS-FET. Graph 304 illustrates an example sensor response to 0.5% $H_2$ at room temperature at $V_D$=0.1 Volts (V) with a sensing layer of 1 nm Pt CS-FET with FOTS underneath, as used in the present disclosure. Even though the example of graph 304 can enable detection of hydrogen in ppm levels, this example is also highly sensitive to relative humidity changes, which makes this example a good candidate to prove the techniques used for the gas sensor 102 of the present disclosure.

Figure 4:
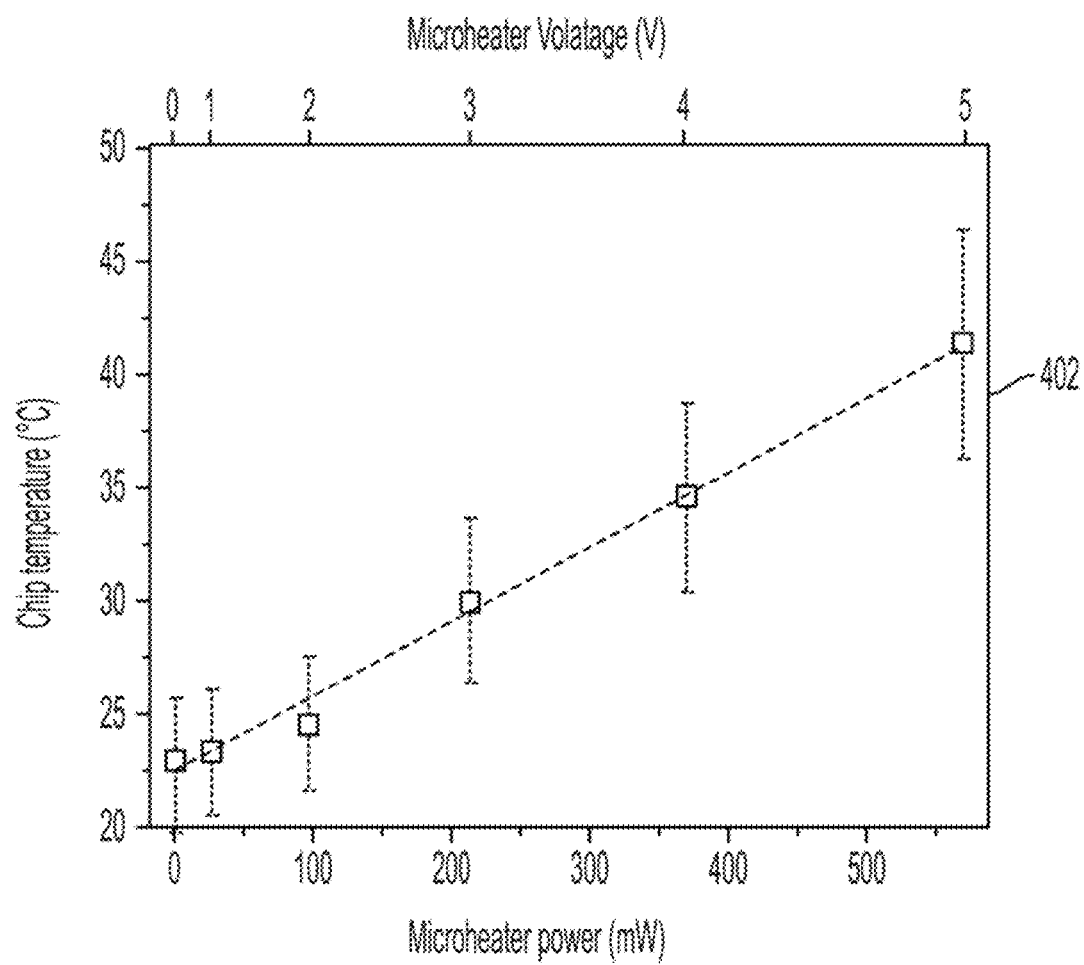
FIG. 4 illustrates an example chart that plots chip temperature vs micro-heater power of the present disclosure.

One method to achieve negligible cross-sensitivity to relative humidity change with the CS-FET platform operates the micro-heaters 104 in a constant voltage mode, such that the chip (e.g., the gas sensors 102 formed on the substrates 108, as described above) is at a temperature level that is slightly above room temperature. Infrared imaging of the chip under different micro-heater powers between zero and 560 mW suggests that the chip temperature increases linearly with power, as shown by graph 402 in FIG. 4.

Figure 5:
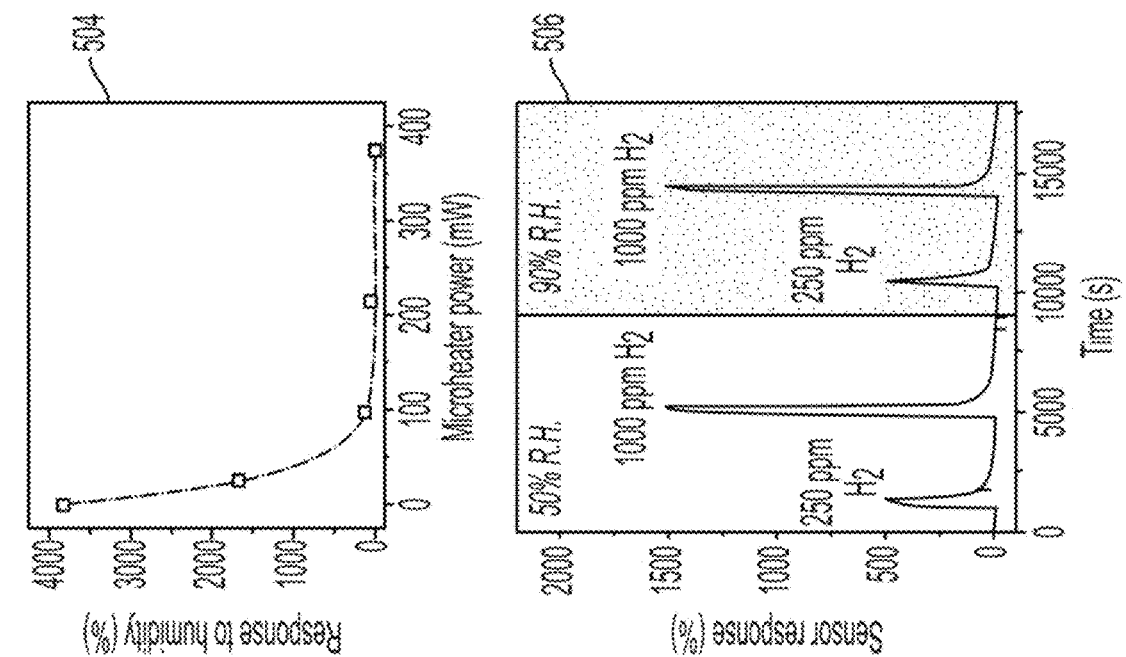
FIG. 5 illustrates example sensor responses of an example gas sensor of the present disclosure to hydrogen gas at various humidity levels.

For a relative humidity change from 50% to 90% with a drain bias of 0.8 V, the CS-FET manifests a response of 3844%, as depicted by graph 502 in FIG. 5. Sensor response is calculated as a percentage change from the baseline current values $(I_{peak}-I_{baseline})/(I_{baseline}) \times 100$. The ambient temperature of the gas sensor 102 is regulated at 25° C., and since relative humidity level was not increased beyond 95%, the chip is operated above the dew point for condensation to occur.

Figure 6:
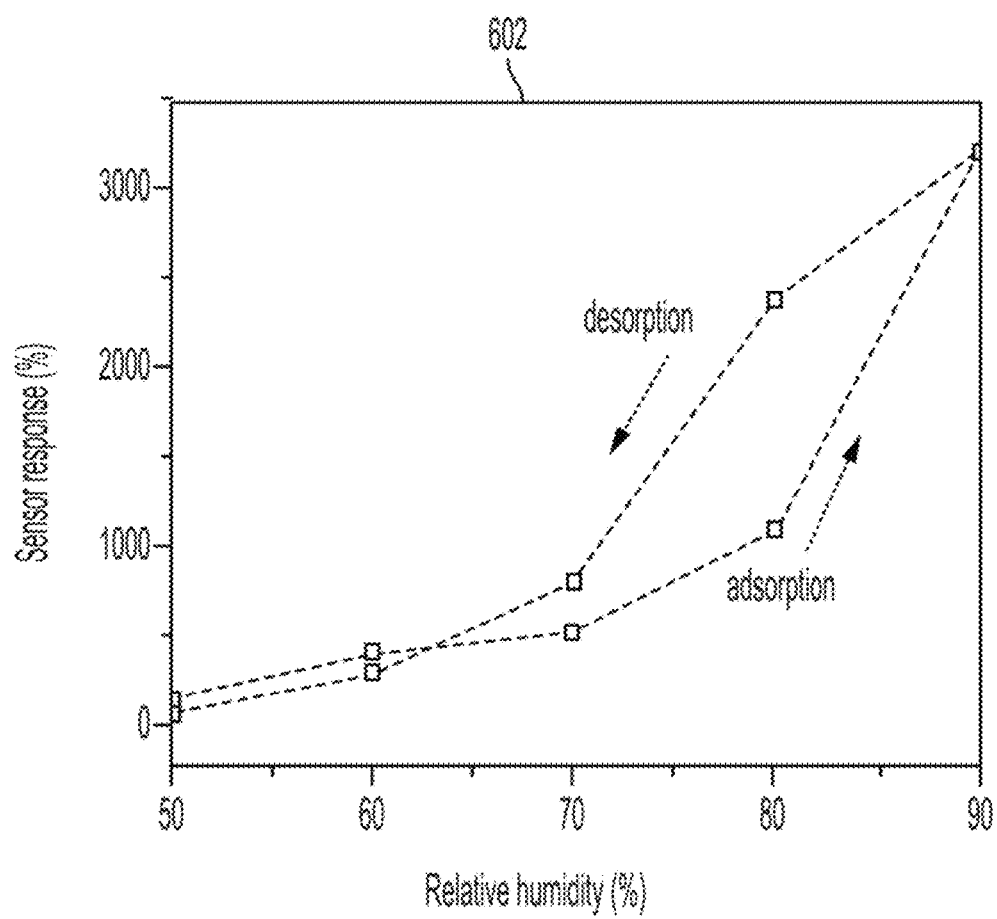
FIG. 6 illustrates an example graph of sensor response versus humidity of the present disclosure.

FIG. 6 illustrates an example graph 602 that illustrates an example plot of sensor response versus humidity. The graph 602 may be extracted from the graph 502 illustrated in FIG. 5, to reveal hysteresis in the adsorption and desorption curves at room temperature, which is a signature of capillary condensation. A schematic of the occurrence of the phenomenon on the nanoparticles is shown in the view 160 in FIG. 1.

To find the approximate relative humidity level at which capillary condensation will occur at room temperature, it may be assumed that the walls of the nanoparticle 164 are much higher in height than the nanoparticle cavity size. The cavity size between most of the nanoparticles 164 may be approximately 2 nm from the view 140 in FIG. 1. The validity of the Kelvin equation for sub-10 nm may be assumed valid for a rough approximation of the relative humidity level that creates onset of capillary condensation 162 shown in view 160 of FIG. 1. An approximate form of the Kelvin equation, as shown in Equation (1) below may be applied:

$$\frac{p_{sat}}{p_v} = \exp\left(\frac{2\gamma V_m \cos\theta}{dRT}\right), \quad \text{Equation (1)}$$

where $p_{sat}$ is the saturated vapor pressure, $p_v$ is the vapor pressure, $\gamma$ is the water surface tension, $V_m$ is the molar volume of water, $\theta$ is the contact angle of water with the nanoparticle wall surface, d is the diameter of the capillary, R is the universal gas constant, and T is the temperature. Given that pure water completely wets contaminants-free platinum, it may be assumed that the platinum nanoparticles are pure in quality and exhibit zero contact angle with water.

Utilizing the standard values of water surface tension as 72 dynes/cm and molar volume of 18 cm$^3$ at room temperature, the value of relative pressure, $p_v/p_{sat}$ which is equivalent to relative humidity, may be calculated to be 59%, which indicates condensation between the cavities formed in the nanoparticle assembly below the dew point pressure.

Figure 7:
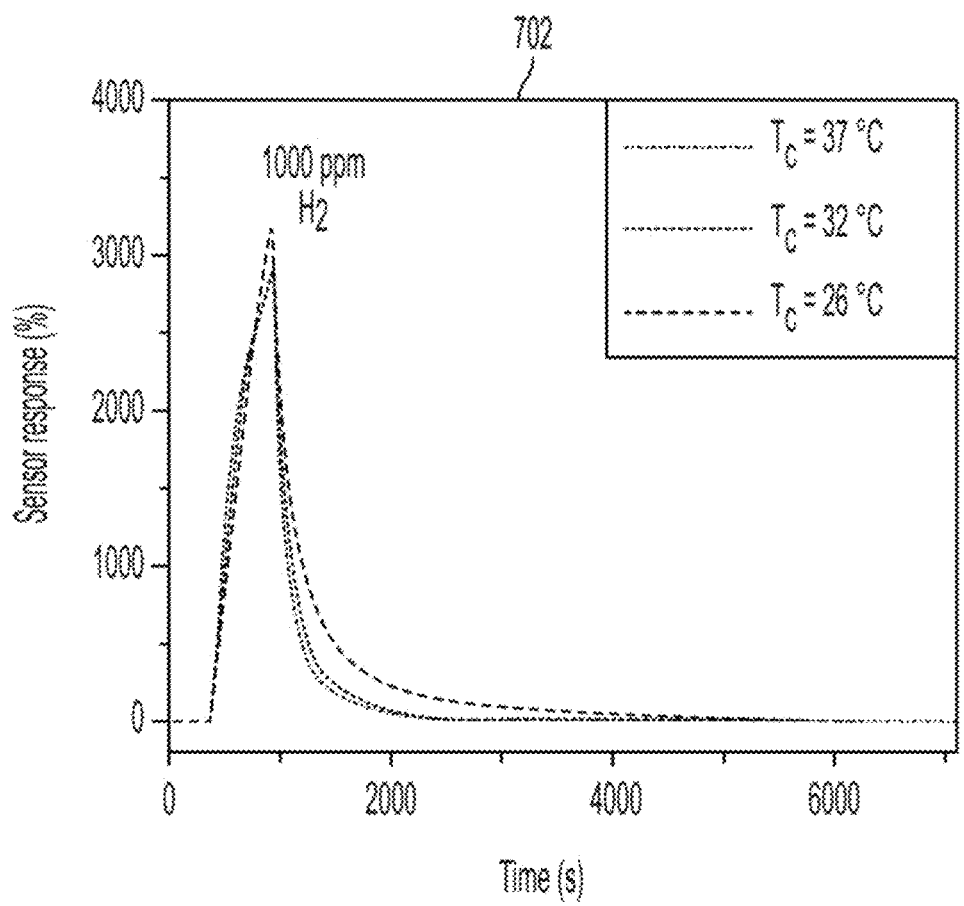
FIG. 7 illustrates an example graph that illustrates an effect of heaters on gas sensor response of the present disclosure.

However, with increasing micro-heater power, the sensor response to this relative humidity change decreases exponentially, as shown by the graph 504 in FIG. 5, with negligible sensor response of 11.6% at a power of 372 mW and corresponding chip temperature of 37±3° C. The evaporation rate of any condensed water tends to increase as the surface temperature is increased. Additionally, the physisorption rate of water molecules on the sensing layer 106 may decrease with increasing chip temperature (which can be explained by Le Chatelier's principle), given adsorption is an exothermic reaction. For the same reason, the overall hydrogen response may also decrease with increasing chip temperature, as shown by a graph 702 illustrated in FIG. 7. However, the decrease in overall hydrogen response may be offset by the elimination of the humidity response. Relatively low chip temperatures (below <100° C.) may eliminate response to humidity because water can be evaporated instead of being boiled-off. In addition, the high surface-to-volume ratio of the nanoparticles 164 allows for a high evaporation rate, unlike the active 'thick' films in MOS and field effect transistors.

Figure 8A:
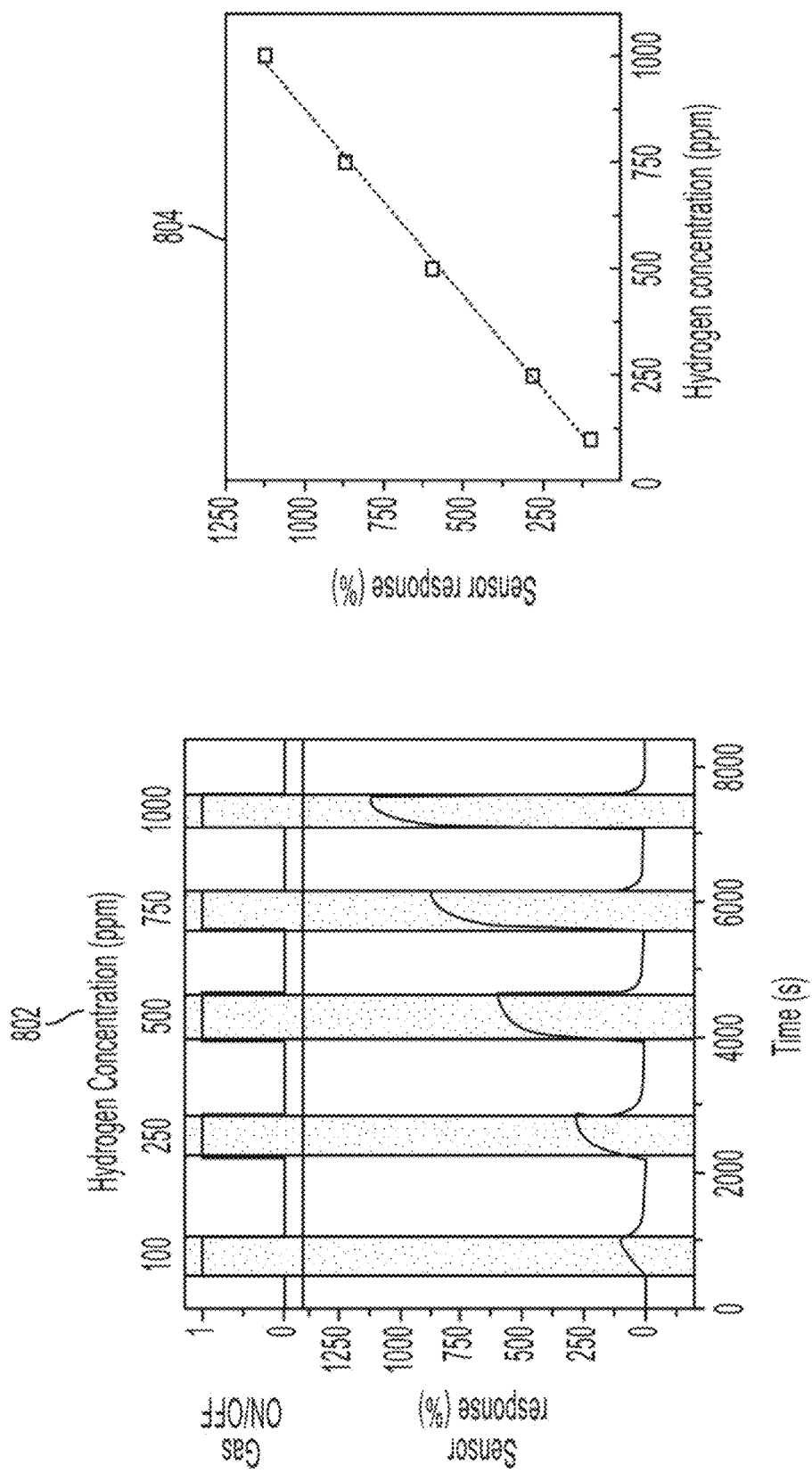
FIGS. 8A-8D illustrate example graphs of various characteristics of the gas sensor of the present disclosure to various concentrations of hydrogen gas.

Additionally, minor reductions in sensitivity to hydrogen may be achieved in relative humidity levels of 50% and 90% with sensor responses of 490% (250 ppm) and 1488% (1000 ppm), and 464% (250 ppm) and 1539% (1000 ppm), respectively, as shown in the graph 506 in FIG. 5. This measurement may be carried out with a different CS-FET sensor with 0.65 V of drain bias (to match the baseline current with the CS-FET with 0.8 V drain bias), for which chip temperature to eliminate humidity response may be 64±8° C. The concentrations of 250 ppm and 1000 ppm of hydrogen may be chosen for these tests because of the linear sensor characteristics observed between 100 ppm and 1000 ppm, illustrated in graphs 802 and 804 of FIG. 8A. For example, the graph 802 illustrates the example sensor response at various concentrations of hydrogen gas. The graph 804 illustrates the sensor response versus various concentrations of hydrogen gas. The graphs 802 and 804 allow for the hypothesis that the sensitivity (e.g., sensor response per ppm) is constant between the concentration levels of the hydrogen gas. Measurements shown in the graph 802 may be performed with a chip temperature of 37±3° C. to eliminate the response to humidity change.

Figure 8B:
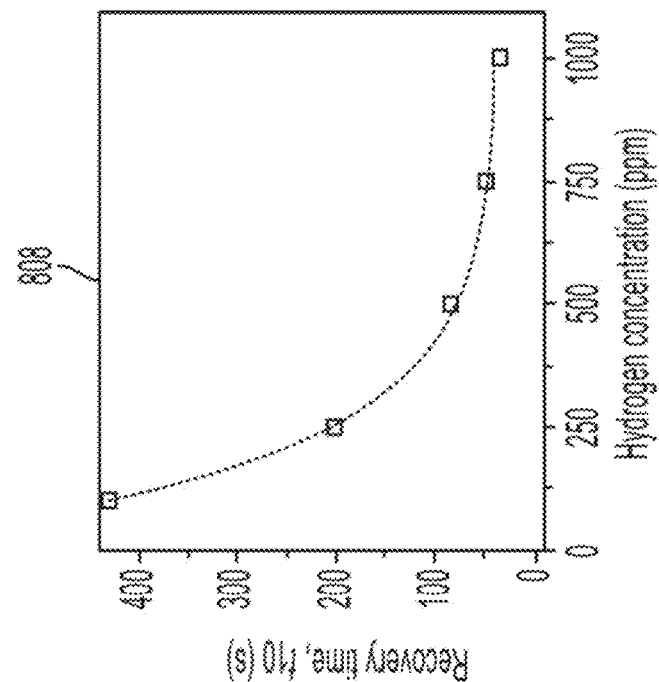
Figure 8B:
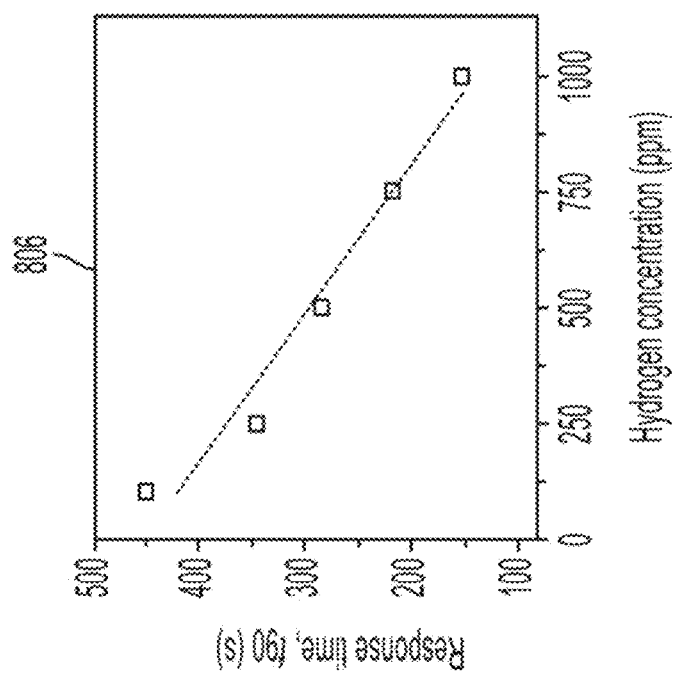

The trends of response ($t_{90}$) and recovery ($t_{10}$) times with varying hydrogen concentration are depicted in graphs 806 and 808 of FIG. 8B. In graph 806, the symbol $t_{90}$ is the time taken for the sensor to reach 90% of its peak response value from the baseline current. The symbol $t_{10}$ is the time taken for the sensor to recover to 10% of its baseline current from the peak value.

Figure 8C:
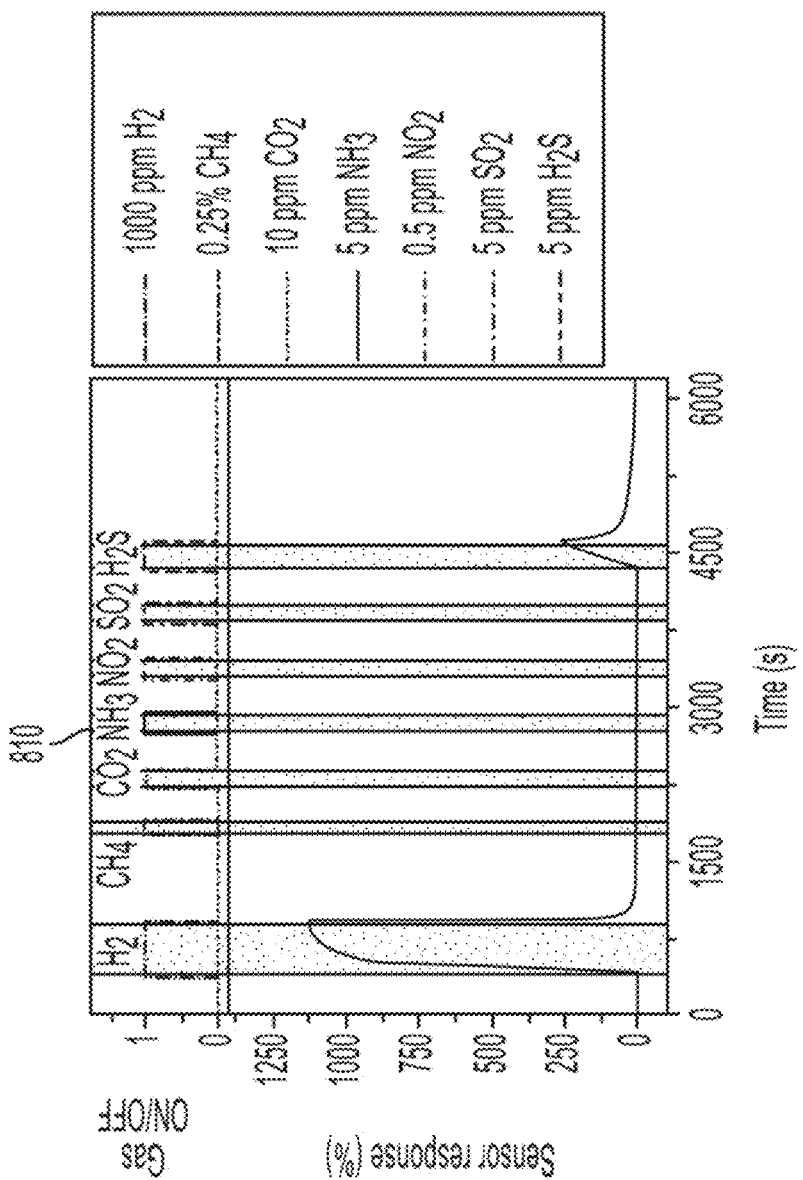
Figure 8D:
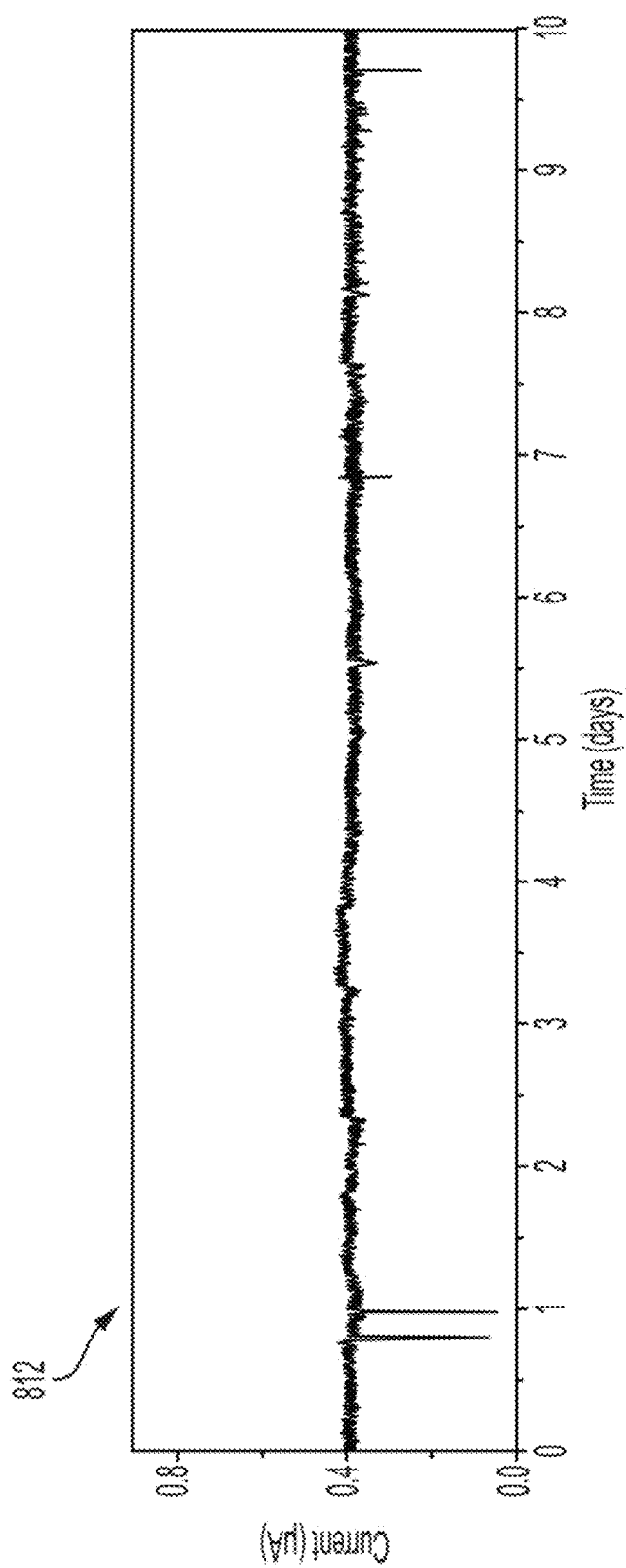

In FIG. 8C, the graph 810 shows that the sensor proves to be highly selective against other gases such as methane, carbon dioxide, ammonia, nitrogen dioxide and sulfur dioxide, though not against hydrogen sulfide. The graph 812 in FIG. 8D illustrates chip temperature over time with the micro-heater 104 switched on for ten days and the chip temperature held at 51° C.±6° C. The graph 812 shows that the temperature exhibits negligible drift, which implies that the active material in the sensor layer 106 remains intact and is unaffected by continuous heater operation.

Figure 9:
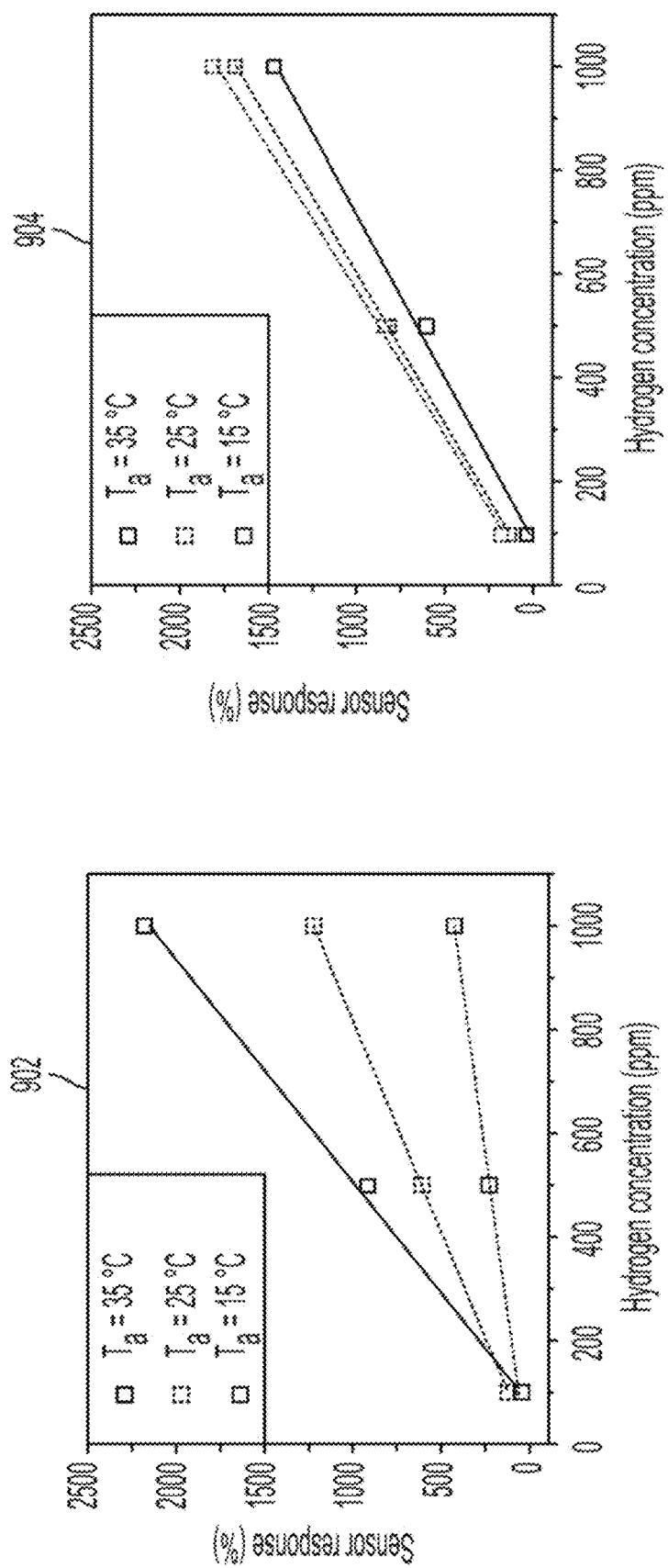
FIG. 9 illustrates example graphs of sensor response of the gas sensors of the present disclosure to hydrogen gas with the micro-heaters on and off.

In one embodiment, an additional advantage of using the micro-heaters 104 is the insignificant variation in gas sensitivity with changing ambient temperature. FIG. 9 illustrates graphs 902 and 904. The graph 902 illustrates the sensor response of the gas sensor 102 with the micro-heaters 104 turned off. The graph 904 illustrates the sensor response of the gas sensor 102 with the micro-heaters 104 turned on.

In one embodiment, three pulses of hydrogen gas with concentration of 100 ppm, 600 ppm and 1000 ppm may be injected in ambient temperatures of 15° C., 25° C. and 35° C. with a drain bias of 0.6 V. It may be seen that the sensitivity decreases by around 5 times as ambient temperature is lowered by 20° C., from 2.2%/ppm at 35° C. to 0.4%/ppm at 15° C., as shown in the graph 902.

However, when the micro-heaters 104 were kept switched-on at a power of 372 mW (chip temperature of 35±3° C.), the sensitivity remains roughly constant (1.6%/ppm at 35° C., 1.7%/ppm at 25° C. and 1.8%/ppm at 15° C., as demonstrated in graph 904). In one embodiment, the benefit of maintaining the constant sensitivity regardless of the ambient temperature may dramatically simplify the calibration process and ensure detection of low concentration levels as the ambient temperature lowers. This may allow the gas sensor 102 of the present disclosure to be deployed for practical usage.

Figure 10:
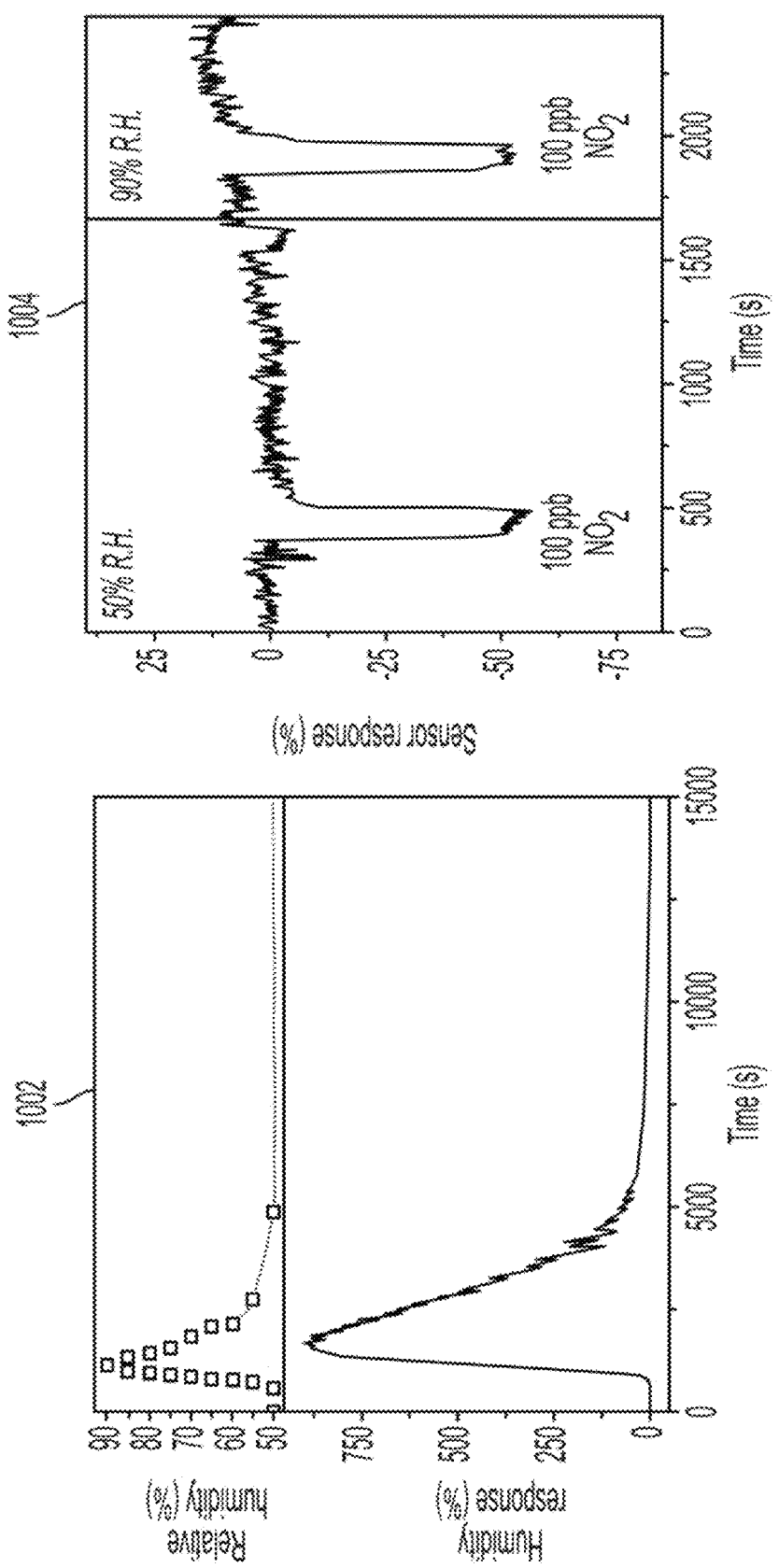
FIG. 10 illustrates example graphs of sensor response of the gas sensors of the present disclosure to nitrogen gas.

In addition to demonstrating humidity selective hydrogen detection using the Pt/FOTS system, the gas sensor 102 of the present disclosure may use active sensing materials for other gases with the CS-FET platform. FIG. 10 illustrates graphs 1002 and 1004 that demonstrate the ability of the gas sensor 102 to detect nitrogen gas. For example, the graph 1002 demonstrates that the CS-FET, with drain bias as 4 V and $InO_x$ thin film (e.g., approximately 1.5 nm) as active material, responds by 895% to relative humidity change from 50% to 90%. With the micro-heaters 104 turned on to keep the chip temperature at 70±8° C., the gas sensor 102 shows negligible sensor response to the humidity change along with constant sensor response (−56% and −52% to 100 ppb $NO_2$ in the humidity levels of 50% and 90%, respectively). An illustration of the negligible sensor response is shown in the graph 1004.

In conclusion, the present disclosure demonstrates that by using the micro-heaters 104 to keep the temperature of the CS-FET slightly higher than the ambient temperature by utilizing the micro-heaters 104, the effects of relative humidity change can be eliminated. Added benefits of constant gas sensitivity using this technique in different ambient temperatures have also been shown in the present disclosure. The results are shown herein using Pt/FOTS as active material for hydrogen sensing and its application to $InO_x$ for nitrogen dioxide sensing.

The micro-heater material and design may be optimized for various applications. For example, it is expected that the power needed to reach the chip temperature levels required to eliminate humidity response may be lower for different materials, thereby extending the applicability of this technique to gas sensors in consumer electronics. As noted above, a temperature sensor may also be fabricated on the same chip, so that the micro-heaters 104 can be looped with a proportional-integral-derivative (PID) controller to maintain constant chip temperature irrespective of ambient temperature for constant sensor responses to same gas concentration level.

Although the present disclosure provides examples for the sensing layer to detect various gases, such as hydrogen and nitrogen dioxide, it should be noted that other sensing materials may be used for other gases. As long as the micro-heaters 104 are used to maintain a desired temperature above room temperature, different sensing materials may be used to detect different types of gases.

In one embodiment, to perform the measurements of the values described herein, the CS-FET device chips may be wire bonded to a 84-pin J-bend leaded chip carrier. Pure dry air may be used as diluent gas. For $H_2$ (e.g., FIGS. 5, 8, and 9) and $NO_2$ (e.g., FIG. 10) sensing experiments, 1% $H_2$ in $N_2$ (Gasco) and 1 ppm $NO_2$ (Gasco) in $N_2$ may be used as sources, respectively. Selectivity measurements in the graph 810 of FIG. 8 may be performed with 2.5% $CH_4$, 100 ppm $CO_2$, 50 ppm $NH_3$, 5 ppm $NO_2$, 50 ppm $SO_2$ and 50 ppm $H_2S$ in $N_2$ (Mesa gas) as sources. Typical gas flow rates may be from 1 to 100 sccm, and diluent (air) flow rate may be approximately 1000 sccm. Gas delivery may be controlled by mass flow controllers (Alicat Scientific Inc.).

Measurements involving relative humidity and temperature changes may be done in an ESPEC Humidity and Temperature Cabinet LHU-113 with a gas outlet 1-2 cm from the sensor chip, otherwise in a walk-in fumehood. CS-FET sensors may be biased using a Keithley 428 current preamplifier, and the current signals may be acquired using a LabVIEW-controlled data acquisition unit (National Instruments, NI USB-6211). The micro-heaters may be powered by the Agilent E3631A DC Power Supply, and all of the measurements may be performed with micro-heaters placed on the adjacent die to the one with the CS-FET.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A gas sensor, comprising:
   a substrate;
   an isolation region formed on outer edges of the substrate;
   a micro-heater formed on the isolation region;
   a sensing layer formed on the substrate inside of the isolation region; and
   a source and drain formed around the sensing layer and inside of the isolation region.

2. The gas sensor of claim 1, wherein the micro-heater comprises a layer of tungsten.

3. The gas sensor of claim 2, wherein the layer of tungsten comprises approximately 200 nanometers.

4. The gas sensor of claim 1, wherein the sensing layer comprises platinum nanoparticles on trichloro (1H,1H,2H,2H-perfluorooctyl) silane (FOTS) for a hydrogen sensor.

5. The gas sensor of claim 4, wherein the platinum nanoparticles in the sensing layer are approximately 1 nanometer thick.

6. The gas sensor of claim 1, wherein the sensing layer comprises indium oxide particles for a nitrogen oxide sensor.

7. The gas sensor of claim 6, wherein the indium oxide particles in the sensing layer are approximately 1.5 nanometers thick.

8. The gas sensor of claim 1, wherein the source and drain each further comprise nickel and tungsten contacts.

9. The gas sensor of claim 1, wherein the micro-heater is powered with a constant voltage to heat the gas sensor to a temperature that is above a room temperature.

10. The gas sensor of claim 9, wherein the temperature comprises approximately 37 degrees Celsius+/−3 degrees.

11. The gas sensor of claim 9, wherein the micro-heater is operated at a power of approximately 372 milliWatts (mW).

12. The gas sensor of claim 1, wherein a drain bias of approximately 0.6 Volts (V) to 0.7 V is applied to the source and drain.

13. The gas sensor of claim 1, further comprising:
    a controller coupled to the micro-heater to adjust an amount of voltage to the micro-heater in response to an ambient temperature change to maintain the gas sensor at a constant operating temperature.

14. A method for fabricating a gas sensor, comprising:
    providing a substrate;
    forming a silicon dioxide isolation region on outer edges of the substrate;
    doping source and drain regions on the substrate;
    patterning a sensing layer region between the source and drain regions;
    doping the sensing layer region;
    defining source and drain contacts on the source and drain regions, wherein each of the source and drain contacts comprises a layer of nickel and tungsten;
    forming a tungsten micro-heater on the silicon dioxide isolation region; and
    depositing a sensing layer on the sensing layer region.

15. The method of claim 14, wherein the sensing layer comprises platinum nanoparticles on trichloro (1H,1H,2H,2H-perfluorooctyl) silane (FOTS) for a hydrogen sensor or indium oxide particles for a nitrogen oxide sensor.

* * * * *